United States Patent [19]

Van't Hof

[11] Patent Number: 5,801,151

[45] Date of Patent: Sep. 1, 1998

[54] ESTIMATION OF OVULAR FIBER PRODUCTION IN COTTON

[75] Inventor: Jack Van't Hof, Brookhaven, N.Y.

[73] Assignee: Associated Universities, Inc., Washington, D.C.

[21] Appl. No.: 761,470

[22] Filed: Dec. 6, 1996

[51] Int. Cl.$^6$ ................. C12Q 1/08; A01N 43/04
[52] U.S. Cl. ............. 514/23; 435/1.1; 435/40.5; 435/378; 435/379; 435/427
[58] Field of Search ................. 435/1.1, 40.5, 435/378, 379, 427; 514/23

[56] References Cited

U.S. PATENT DOCUMENTS

| | | | |
|---|---|---|---|
| 2,749,796 | 6/1956 | Bauer | 88/14 |
| 3,712,746 | 1/1973 | Bergeron | 356/256 |
| 3,829,216 | 8/1974 | Persidsky | 356/36 |
| 5,087,120 | 2/1992 | Anthony | 356/36 |
| 5,349,436 | 9/1994 | Fisch | 356/246 |
| 5,402,240 | 3/1995 | Thistlethwaite et al. | 356/434 |
| 5,437,697 | 8/1995 | Sebastian et al. | 47/58 |

OTHER PUBLICATIONS

Second Annual Fiber Forecast: The Only Pre–Harvest Mid–South Crop Data Report Fiber, p. 4, Oct. 1995.

A Quantitative Procedure for Estimating Cotton Fiber Growth, Stain Technology, p. 85, vol. 49 No. 2, 1974.

*Primary Examiner*—Nathan M. Nutter
*Attorney, Agent, or Firm*—M. C. Bogosian

[57] ABSTRACT

The present invention is a method for rendering cotton fiber cells that are post-anthesis and pre-harvest available for analysis of their physical properties. The method includes the steps of hydrolyzing cotton fiber cells and separating cotton fiber cells from cotton ovules thereby rendering the cells available for analysis. The analysis of the fiber cells is through any suitable means, e.g., visual inspection. Visual inspection of the cells can be accomplished by placing the cells under an instrument for detection, such as microscope or other means.

24 Claims, 4 Drawing Sheets

ESTIMATION OF OVULAR FIBER PRODUCTION IN COTTON

This invention was made with Government support under contract number DE-AC02-76CH00016, awarded by the U.S. Department of Energy. The Government has certain rights in the invention.

FIELD OF THE INVENTION

The present invention relates to a method for rendering fibrous plant cells available for analysis of their physical properties, and more particularly to rendering cotton fiber cells available for physical analysis.

BACKGROUND OF THE INVENTION

Generally, a large percentage of consumers' expenditures are for clothing. This has created a market that is unmatched for textiles in the world. About two thirds of the basic raw materials required by textile manufactures are cotton supplies. This is because fibers obtained from cotton plants are versatile and comparatively low in cost to produce and to manufacture into finished products. Thus, the cotton plant has become a very important agricultural crop throughout the world.

Because cotton is a major agricultural crop, growers are constantly seeking ways to increase plant production and fiber quality. Thus, increasing the productivity or "yield" of the cotton plant, and the quality of the fibers, is a major goal in cotton production.

Attempts have been made to determine yield and fiber quality in crop plants in general. U.S. Pat. No. 5,437,697 issued to Sebastian et al. discloses a method for identifying genetic markers that are linked to agronomically important genes. However, this method is time consuming and expensive because it requires conducting a genetic marker survey to determine the genotypes of the plants.

Attempts for predicting the yield of cotton plants by estimating the number of fiber cells per cotton ovule have also been disclosed in literature. (*Second Annual Fiber Forecast: The Only Pre-Harvest Mid-South Crop Data Report*, Fiber, p. 4, October 1995; *Down The Row*, Fiber, p. 6, October 1995; *Plant Population Determines Harvest*, Fiber, p. 9; October 1995; *The 1995 Mid-South Fiber Forecast*, Fiber, p. 10, October 1995.) These methods, however, for estimating the amount of fibers per ovule rely on indirect steps for ascertaining the number of fiber cells per ovule, which is in part due to the inability to directly analyze the fiber cells. This in turn detrimentally affects the degree of accuracy of predictions made from the data collected. Moreover, these methods are ineffective for predicting the quality of the crop early in the crop growing season because they are done late in the season, i.e., at harvest time.

At the present time, known procedures for counting fiber cells on young cotton ovules (i.e., ovules prior to harvest) require the utilization of electron microscopy. This in turn requires an elaborate electron microscope laboratory, extensive sample preparation, and complex data acquisition procedures. Moreover, these procedures suffer from the disadvantage that only a small portion of a single ovule at a time can be analyzed. As will be apparent to those skilled in the art, electron microscopy is also quite labor intensive.

Thus, there is a need in the art for a method for rendering cotton fiber cells available for direct analysis of their physical properties, such as the counting and physical characterization of the cells. Moreover, there is a need for a method of estimating the yield and quality of cotton fiber cells from young ovules that is simple and inexpensive.

Accordingly, it is an object of the present invention to provide a method for rendering cotton fiber cells available for analysis of their physical properties early in the crop growing season (e.g., months before harvest). It is also an object of the present invention to provide a method that is simple and inexpensive for estimating the potential yield and quality of cotton fibers before harvest.

SUMMARY OF THE INVENTION

The present invention is a method for rendering cotton fiber cells that are post-anthesis and pre-harvest available for direct analysis of their physical properties. The method includes the steps of hydrolyzing the cotton fiber cells on the ovules and thereafter separating cotton fiber cells from the cotton ovules thereby rendering the cells available for direct analysis. The analysis of the cotton fiber cells is typically done by visual inspection, such as analyzing the cells through the use of microscopy, or through the use of other detection means.

The hydrolysis of the fiber cells on the ovules involves (i) treating the ovules with a primary acid solution under reaction conditions effective to hydrolyze the intercellular connections between the cells on the ovules; and (ii) treating the cells with a sulfur-containing reagent under reaction conditions effective to increase the flexibility of the cells.

Preferably, the acid for the primary acid solution is an inorganic acid having a pKa of at least about 7. Examples of suitable acids include, but are not limited to, inorganic acids such as $HNO_3$, $H_2SO_4$, $HClO_4$, and HCl, in which HCl is preferred. An acid having a pKa less than 7 can also be utilized in conjunction with heating the primary acid solution.

Examples of suitable sulfur-containing reagents include, but are not limited to, $K_2S_2O_5$ (i.e., meta-bisulfite) and sulfur dioxide, in which meta-bisulfite is more preferred.

In an optional embodiment of the present invention, the hydrolysis of the ovules can also involve treating the cotton ovules with a secondary acid solution before or after the treatment of the ovules with the primary acid solution. The ovules are treated with the secondary acid solution under reaction conditions effective to hydrolyze the intracellular contents of the cotton fiber cells.

The acid for the secondary acid solution is preferably an acid having a pKa less than the acid for the primary acid solution. Preferably, the pKa for the acid of the secondary acid solution is at least about 4. Examples of suitable acids include, but are not limited to, acids such as propanoic acid, lactic acid, formic acid, and glacial acetic acid, in which glacial acetic acid is more preferred.

After the hydrolysis of the fiber cells with the primary acid solution, the fiber cells are then separated from the ovules. The separation of the cells from the ovules is typically achieved by physical agitation. Once separated, the fiber cells are then available for analysis.

In more preferred embodiment of the present invention, the cotton fiber cells are fixed (i.e., killed and preserved) with a fixative solution prior to separating the fiber cells from the cotton ovules, which is before or after hydrolysis of the cells. The fixative solution is a mixture of an alcohol and an acid. Suitable alcohols for the fixative solution are alcohols having less than four carbon atoms. These include, but are not limited to, methanol, ethanol and propanol, in which ethanol is more preferred. Suitable acids for the fixative solution are acids having a pKa of at least about 4, e.g., from about 4 to about 5. These preferably include, but are not limited to, propanoic acid, lactic acid, formic acid and glacial acetic acid, in which glacial acetic acids more preferred. The ratio of the mixtures of the alcohol to acid is from about 10:1 to about 1:10, preferably from about 5:1 to about 1:3, and more preferably about 3:1 to about 1:1.

In alternative embodiment of the present invention, the separation of the cotton fiber cells from the ovules is accomplished by first removing cotton plant embryos from the hydrolyzed ovules and then isolating the cotton fiber cells from the remaining ovules whereby the cells are made available for analysis. The isolation of the fiber cells from the cotton ovules is also achieved in the same manner as previously described in the separation step.

In a more preferred embodiment of the present invention, the cotton fiber ovules are optionally treated with a tertiary acid solution prior to separating fiber cells from the ovules. The acid for the tertiary acid solution is preferably an acid having a pKa of at least about 3, e.g., from about 3 to about 6. Examples of acids for the tertiary acid solution include, but are not limited to, propanoic acid, lactic acid, acetic acid, and citric acid in which acetic acid is more preferred.

Once separated, the physical properties of the fiber cells can be directly analyzed. Typically this is accomplished by visual inspection. For example visual inspection can involve the steps of (i) placing the cotton fiber cells under a microscope; and (ii) observing the physical properties of the cotton fiber cells. However, the cells can also be labeled or stained to improve analysis or to facilitate analysis by other detection means.

Advantageously, as the result of the present invention, cotton fiber cells can be isolated from very young cotton plants for direct analysis. Specifically, the physical properties of crops can be determined before harvest when the ovules are as young as 2 to 4 days post anthesis (dpa). This in turn allows the crop grower to predict the potential yield and quality of the crop early in the season. Thus, the present invention provides a simple and inexpensive method of rendering cotton fiber cells available for analysis of their physical properties, which offers a high degree of accuracy to the skilled artisan in predicting the crop yield and quality.

For a better understanding of the invention, reference is made to the following description and examples, the scope of which is pointed out in the appended claims.

DETAILED DESCRIPTION OF THE INVENTION

The present invention is a method for rendering cotton fiber cells that are post-anthesis and pre-harvest available for direct analysis of their physical properties. The method includes hydrolyzing the cotton fiber cells on the ovules and separating cotton fiber cells from the ovules thereby rendering the fiber cells available for direct physical analysis. As a result of the present invention, cotton fiber cells can now be isolated from cotton plants while in the field, and have their physical properties analyzed as early as 2 to 4 days post anthesis (dpa).

The physical properties of crops that can be determined include (1) the number of fiber cells per ovule, (2) the diameter of fiber cells, (3) the gross cell wall characteristics of the fiber cells, (4) the shape of the fiber cells, (5) the relative proportions of fiber cell sub-populations within the total fiber cell population on an ovule. As will be apparent to the skilled artisan, ascertaining the above properties provides important information which will assist the crop grower, inter alia, in predicting the potential yield from the crop.

The hydrolysis of the cotton ovules involves (i) treating the ovules with a primary acid solution under reaction conditions effective to hydrolyze the intercellular connections between the cells on the ovules; and thereafter (ii) treating the fiber cells with a sulfur-containing reagent under reaction conditions effective to increase the flexibility of the cells.

The term "treating" is meant to refer any means by which the components of a particular step are brought into intimate contact with each other. Typically, as illustrated below, treating is accomplished by immersing the product to be treated in the specific reagent for that step. However, any other suitable means known in the art can also be utilized.

In accordance with the present invention, the intercellular connections of the fiber cells are hydrolyzed with the primary acid solution. Accordingly, the primary acid solution must be of suitable strength to effectively hydrolyze the intercellular connections between the cells. Typically, the acid for the primary acid solution is an inorganic acid having a pKa of at least about 7, and preferably from about 7 to about 8. Examples of acids for the primary acid solution include, but are not limited to, $HNO_3$, $H_2SO_4$, $HClO_4$, and HCl, in which HCl is more preferred. Alternatively, an acid having a pKa less than 7 can be utilized if the reaction medium is heated. As will be apparent to those skilled in the art, the actual concentration (i.e., molarity or normality) of the acid solution is variable.

The amount of time necessary to facilitate hydrolysis is primarily dependent on the strength of the acid solution. The ovules can be treated with the primary acid solution (e.g., immersed) at room temperature for about 1 to about 3 days. However to facilitate the hydrolysis process, the ovules can be heated in the primary acid solution at a temperature of about 22° C. to about 100° C., preferably of about 65° C. to about 100° C., and more preferably of about 95° C. to about 100° C. The amount of time necessary to heat the cotton ovules to hydrolyze the intercellular connections of the cotton fiber cells in the primary acid solution is from about 5 minutes to about 120 minutes, preferably from about 10 minutes to about 30 minutes, and more preferably from about 10 minutes to about 20 minutes. However, as will be apparent to one of ordinary skill in the art all of the above described parameters can easily be varied in accordance with the present invention.

It is believed that a reasonable indicator of effective hydrolysis occurring is a color change of the ovules being treated. For example, if HCl is utilized as the acid for the primary acid solution the appearance of a burgundy color is believed to indicate sufficient hydrolysis. However, the color and intensity will vary with the choice of acid.

After treating with the primary acid solution, the ovules and fiber cells are then treated with a sulfur-containing reagent. Examples of suitable sulfur-containing reagents include, but are not limited to, $K_2S_2O_5$ (i.e., meta-bisulfite) and sulfur dioxide, in which meta-bisulfite is more preferred. It is believed that the sulfur-containing reagent strengthens the cell wall of the fiber cells by cross-linking the polysaccharide material of the cell wall. Moreover, an acid such as HCl can also be added to the solution to facilitate cross-linking. The cross-linking of the cell wall in turn is believed to make the fiber cells more flexible, and decrease the possibility of the cells rupturing during separation. As will be appreciated by the skilled artisan, the recovery of more intact cells results in a more accurate cell count.

At a minimum, the ovules and fiber cells can be treated with the sulfur-containing reagent at room temperature. Typically, this involves immersing the ovules/fiber cells in a solution containing the reagent from about 1 to about 3 days. However, to decrease the time period to strengthen the cells, the mixture can be heated from about 2 minutes to about 72 hours at about 22° C. to about 100° C., preferably from about 15 minutes to about 180 minutes at about 22° C. to about 100° C., and more preferably for about 2 minutes at about 95° C. to about 100° C. Moreover, one can vary the concentration of the sulfur-containing reagent and of the acid. All of these parameters can easily be varied by one skilled in the art in accordance with the method of the present invention.

In an optional embodiment of the present invention, the hydrolysis of the ovules can also involve treating the cotton ovules with a secondary acid solution before or after the treatment of the ovules with the primary acid solution. Preferably, this is done before hydrolysis with the primary acid solution. The ovules are treated with the secondary acid solution under reaction conditions effective to hydrolyze the intracellular contents of the fiber cells. The use of the secondary acid solution facilitates the subsequent analysis of the contents of the fiber cells. However, this step is unnecessary if one only desires to ascertain the quantity of fiber cells on the ovule.

The secondary acid solution should be of sufficient strength to hydrolyze the cellular contents of the cells, but not the intercellular connections between the cells. Typically, the acid for the secondary acid solution is an acid having a pKa of at least about 4, and preferably from about 4 to about 5. Examples of suitable acids for the secondary acid solution include, but are not limited to, propionic acid, lactic acid, formic acid, and glacial acetic acid in which glacial acetic acid is preferred. The actual concentration of the acid solution is variable, which can easily be ascertained by one skilled in the art with the other reaction parameters.

The temperature and time parameters are also variable and primarily depend on the strength of the secondary acid solution. At a minimum, the ovules can be treated in secondary acid solution at room temperature for about 1 to about 3 days. However, to facilitate intracellular hydrolysis, the ovules can be heated in the secondary acid solution at a temperature of about 40° C. to about 100° C., preferably of about 90° C. to about 100° C., and more preferably of about 95° C. to about 100° C. The amount of time necessary to heat the cotton ovules in the secondary acid solution is, respectively, from about 5 to about 60 minutes, preferably from about 10 to about 30 minutes, and more preferably from about 10 to about 15 minutes.

After the hydrolysis of the cotton fiber cells, the cells are then separated. The separation of the cotton fiber cells from the ovules can be accomplished by any suitable means known in the art. Typically, this is accomplished by physically agitating the fiber cells and the ovules. Thus, the removal of the fiber cells can be accomplished manually by the technician, or by other physical means (e.g., vortexing).

In another embodiment of the present invention, the cotton fiber cells can be fixed before or after the hydrolysis of the intercellular connections, but prior to separating the cotton fiber cells from the cotton ovules. Preferably, the cells are fixed prior to hydrolysis since the fixative solution is primarily utilized to kill and preserve the cells for subsequent analysis. The fixation of the cells is also believed to strengthen the fiber cells prior to being separated from the ovules. The step is accomplished by treating the cells with the fixative solution, e.g., immersing the cotton ovules and cells in the fixative solution.

The fixative solution is a mixture of an alcohol and an acid, which is well known in the art. Suitable alcohols for the fixative solution are alcohols having less than four carbon atoms. These include, but are not limited to, methanol, ethanol and propanol, in which ethanol is more preferred. Suitable acids for the fixative solution are acids having a pKa of at least 4, and preferably from about 4 to about 5. These include, but are not limited to, propionic acid, lactic acid formic acid and glacial acetic acid, in which glacial acetic acid is preferred. The concentration of the acid for the fixative solution is variable and can be adjusted by the skilled artisan along with the other parameters of the invention. The ratio of alcohol to acid is about 10:1 to about 1: 10, preferably about 5:1 to about 1:3, and more preferably about 3:1 to about 1:1.

The cells can be treated (e.g., immersed) with the fixative solution for extended periods of time since the fixative solution acts as a preservative. However, the amount of time typically necessary to fix the cells is from about 1 minute to about 60 minutes, preferably from about 2 minutes to about 20 minutes, and more preferably from about 5 to about 10 minutes.

In an alternative embodiment of the present invention, the separation of the cotton fiber cells from the ovules is accomplished by first removing cotton plant embryos from the ovules and then isolating the cotton fiber cells from the remaining cotton ovules. The purpose of removing the embryos from the ovules and subsequently isolating of the fiber cells from the remaining ovules is to identify the location of different subpopulations of fiber cells on the ovules. The separation of the fiber cells from the cotton ovules can be achieved by suitable methods known in the art.

In a more preferred embodiment, the step of separating cotton fiber cells from the ovules can further include treating the ovules with a tertiary acid solution prior to separating the fiber cells from the ovules. It is believed that the tertiary acid solution maintains the separation of the cells once their intercellular connections have been hydrolyzed with the primary acid solution. Moreover, it is believed that this step enhances subsequent staining or labeling of the fiber cells.

In terms of relative strength, the tertiary acid solution can be weaker than the secondary acid solution. Thus, the acid for the tertiary acid solution is preferably an acid having a pKa of at least about 3, preferably from about 3 to about 6. Examples of suitable acids include, but are not limited to, citric acid, propionic acid, lactic acid, acetic acid, in which acetic acid is more preferred. The actual concentration of the acid solution is variable. The amount of time to treat the fiber cells can range from 1 minute to 3 days, with 5 to 60 minutes being preferred and 5 to 15 minutes being more preferred.

Once the cotton fiber cells are separated from the ovules, they can be analyzed to ascertain the number and quality of the fiber cells. The analysis of the fiber cells can be accomplished by any suitable means known in the art. Typically, the analysis is done by visual inspection by a technician. This usually involves the steps of (i) placing the cotton fiber cells under a instrument for detection ( e.g., a microscope); and (ii) observing the physical properties of the cotton fiber cells. From the data ascertained, predictions as to yield or other properties can be readily made. The manipulation of the such data is well within the ability of one of ordinary skill in the art.

It is also contemplated that the method of the present invention can be automated, including the subsequent analysis of the cotton fiber cells. Typically, this would involves the use various labeling agents and detection means for cell analysis. For example, a fluorescent label in conjunction with a modified cell counter can be utilized to automate the quantative analysis of the fiber cells.

Similarly, It is contemplated that the method of the present inventions is applicable to fibrous plants other than cotton. Examples include, but are not limited to, cottonweed and milkweed.

EXAMPLES

The following non-limiting examples illustrate the invention in relation to analyzing the physical properties of cotton fiber cells.

Example 1

This example illustrates that the number of cotton fiber cells per ovule can be determined via the method of the present invention. Three to five bolls were removed from various species of cotton plants leaving about 3 cm of the stems attached. All petals were then removed. The three floral bracts of each of the bolls were folded back to show where they were still attached to the base. The three bracts were then removed by slicing the boll just above where the bracts were attached. A shallow cut was made at the base of the sepals. Sepals were removed by hands. The bolls were then snapped open by hands to reveal the ovules in the locules. Fifteen ovules from each of the bolls were removed for fixing. The ovules were fixed by being immersed in a fixative solution (3:1 ethanol and glacial acetic acid) under a vacuum for approximately 5 minutes.

Five ovules were removed from the fixative solution and placed in an empty, pierced topped 1.5 ml Eppendorf tube. Approximately 500 μl of distilled water was added to the tube. The ovules were soaked in the distilled water for about 5 minutes. The water was removed and 500 μl of glacial acetic acid was added to the tube. The tube was heated in a heating block for approximately 10 minutes at 95° C.–100° C.

The hot glacial acetic acid was removed and about 500 μl of distilled water was added to the tube. The ovules were soaked in the distilled water for about 1 minute. The distilled water was then replaced by 500 μl of 5N HCl. The tube was then placed in the heating block for approximately 20 minutes at 95° C.–100° C. until the ovules were softened and turned burgundy in color.

The 5N HCl was then replaced by 500 μl of distilled water. The distilled water was then replaced by 200 μl of meta-Bisulfite solution (200 ml $H_2O$, 30 ml 1N HCl, and 3 g $K_2S_2O_5$). The ovules were soaked in the meta-Bisulfite solution for about 15 minutes at room temperature. The meta-Bisulfite solution was then removed and the ovules were washed by distilled water. Approximately 500 μl of 45% acetic acid (volume:volume) was added to the tube.

The ovules were crushed against the side of the tube with a 1000 μl tip attached to a microliter pipette. The crushed tissues were then gently drawn and expelled into the microliter pipette tip. Thereafter 500 μl of the fragmented tissue was transferred to a 15 ml glass test tube.

Approximately 500 μl of 45% acetic acid was added to the tube. The cells were repeatedly drawn and expelled until only 5 or so dark red fragments remain. The five remaining fragments were cells surrounding the chalazal plug. Approximately 7 ml of 45% acetic acid was added to the tube bringing the total volume to 8 ml. The tube was capped with Parafilm and then vortexed and/or hand shaken for a second or two.

The cells were dispersed by shaking. Approximately 35 μl of the solution was removed and placed on the platform of a Howard mold counter. The counter was covered with a glass coverslip and the cells were allowed to settle for a minute. The physical properties of the cells were then observed under a light microscope at 125X magnification. The number of cells per ovule was determined and the results are illustrated in Table 1.

TABLE 1

| Cultivar | No. of fiber cells/ovule under optimal condition | No. of fiber cells/ovule under sub-optimal condition | Potential (%) |
|---|---|---|---|
| Acala maxx | 19,804 | 14,437 | +37 |
| DP2 | 12,147 | 6,935 | +75 |
| DP51 | 10,491 | 7,014 | +49 |
| DP5415 | 11,624 | 10,226 | +13 |
| Geor. King | 14,360 | 9,616 | +33 |
| MD51 ne | 14,030 | 10,841 | +29 |
| SG501 | 11,552 | 12,548 | −8 |
| Stoneville 463 | 12,631 | — | — |

From Table 1 it is observed that the number of cotton fiber cells per ovule from plants cultivated under optimal and sub-optimal conditions was determined in accordance with the present invention. Optimal conditions were achieved by continuous fluorescent and incandescent lights and constant temperature of 28° C. in growth chambers. Sub-optimal conditions range from the plants grown in the field to the plants grown in the chambers where both light and temperature were changed during a 24 hour day. As the result of the determination of the number of cells per ovules (from the plants cultivated under optimal and sub-optimal conditions), the potential for fiber production was calculated by utilizing the following formula:

$$potential=[opt].-[sub-opt.]/[sub-opt.]\times 100$$

in which "opt." is the number of fiber cells per ovule from plants grew under optimal condition and "sub-opt." is the number of fiber cells per ovule from plants grew under sub-optimal condition.

The data in Table 1 shows that the potential for increased cells/ovule varies from less than zero to 75% among the plants tested. Thus, through the present invention, the physical properties of the fiber cells can be determined, which allows the skilled artisan to ascertain the potential for increased fiber cells per ovule.

Example 2

In order to ascertain whether the cotton plant having a higher fiber cells per ovule has the dominant gene, cotton plant MD51-5 and cotton plant HQ95-6 were crossed. The number of fiber cells per ovule for cotton plant HQ95-6 and cotton plant MD51-5 were obtained in accordance with the present invention. The resulting offspring produced from the breeding the cotton plant MD51-5 and cotton plant HQ95-6 was F1. The number of fiber cells per ovule for the offspring F1 was also obtained in accordance with the present invention. The number of fiber cells per ovule for the parents and offspring are shown in Table 2.

TABLE 2

| Plant | Number of fiber cells/ovule |
| --- | --- |
| parent MD51-5 | 10,202 |
| parent HQ95-6 | 14,592 |
| F1 | 14,081 |

The data in Table 2 illustrate that the present invention can be utilized to detect genetic differences between the two parental plants and their resulting offspring. Specifically, Table 2 demonstrates that the cotton plant HQ95-6, has more fiber cells per ovule than MD51-5, exhibits genes that are dominant for fiber cell numbers. This was demonstrated when the offspring F1 exhibited a high number of fiber cells that correlates with the number of fiber cells per ovule exhibited by its parent HQ95-6. Thus, Table 2 illustrates use of the present invention to ascertain the expression of genes controlling the number of fiber cells per ovule.

Example 3

Cotton fiber cells were separated from cotton ovules obtained from 41 nursery plants in accordance with the method of the present invention. The plants were grown under sub-optimal field condition (i.e., cold weather and dark conditions). The physical properties of the cotton plants are shown in Table 3 and depicted in FIG. 3.

TABLE 3

| Nursery Plant No. | Cells Per Ovule | Cultivar | S.D. | % Error | DPA | Geno-type |
| --- | --- | --- | --- | --- | --- | --- |
| 15 | 6,032 | DES199 | 409 | 6.80% | 3 | B |
| 73 | 6,179 | Tamcot | 221 | 3.60% | 4 | |
| 5 | 6,635 | CB 1233 | 739 | 11.10% | 3 | |
| 65 | 6,647 | Wan. Cleve. | 664 | 9.90% | 4 | |
| 56 | 6,920 | Express 432 | 1475 | 21.30% | 4 | |
| 6 | 6,935 | Dp. 20 | 831 | 11.90% | 4 | C |
| 24 | 6,957 | HY 39 | 606 | 8.70% | 3 | |
| 8 | 7,014 | Dp. 51 | 729 | 10.30% | 4 | |
| 58 | 7,450 | Hartsville | 651 | 8.70% | 4 | |
| 67 | 7,663 | Acala 44 | 593 | 7.80% | 4 | |
| 7 | 7,724 | Dp. 50 | 99 | 1.30% | 4 | C |
| 61 | 7,766 | Lankart 57 | 432 | 5.60% | 4 | |
| 1 | 7,799 | CB 232 | 769 | 9.80% | 3 | |
| 4 | 7,860 | CB1 135 | 123 | 1.60% | 3 | |
| 14 | 8,100 | Dp. 90 | 261 | 3.20% | 3 | A |
| 22 | 8,233 | Hartz H1560 | 328 | 4.00% | 3 | F |
| 68 | 8,239 | Acala 111 | 70 | 0.80% | 4 | |
| 69 | 8,363 | Acala 1517 | 288 | 3.40% | 4 | |
| 31 | 8,436 | S-35 | 800 | 9.50% | 4 | D |
| 59 | 8,443 | Hopi Moencopi | 341 | 4.00% | 4 | |
| 23 | 8,501 | HS23 | 612 | 7.20% | 3 | |
| 62 | 8,835 | Lone Star | 588 | 6.60% | 4 | |
| 18 | 8,939 | Hartz H1244 | 778 | 8.70% | 4 | E |
| 3 | 8,953 | CB 407 | 271 | 3.00% | 3 | |
| 2 | 9,076 | CB 233 | 203 | 2.20% | 3 | |
| 36 | 9,127 | ST LA887 | 799 | 8.70% | 4 | F |
| 57 | 9,273 | Half & Half | 701 | 7.60% | 4 | |
| 16 | 9,384 | Hartz H1215 | 262 | 2.80% | 3 | E |
| 13 | 9,385 | Dp. X0227 | 580 | 6.20% | 3 | |

TABLE 3-continued

| Nursery Plant No. | Cells Per Ovule | Cultivar | S.D. | % Error | DPA | Geno-type |
| --- | --- | --- | --- | --- | --- | --- |
| 12 | 9,409 | Dp. X0159 | 940 | 9.90% | 3 | |
| 60 | 9,703 | Kakchi | 265 | 2.70% | 4 | |
| 10 | 10,226 | Dp. 5415 | 908 | 8.80% | 3 | |
| 19 | 10,498 | Hartz H1277 | 943 | 9.50% | 3 | |
| 21 | 10,953 | Hartz H1380 | 1492 | 13.60% | 3 | |
| 20 | 10,979 | Hartz H1330 | 784 | 7.10% | 3 | |
| 64 | 11,005 | Tamcot Sp21 | 755 | 6.90% | 4 | |
| 66 | 11,091 | Acala, Young's | 379 | 3.40% | 4 | |
| 11 | 11,303 | Dp. 5690 | 1143 | 10.10% | 3 | |
| 17 | 11,347 | Hartz H1220 | 166 | 1.50% | 4 | E |
| 71 | 11,514 | Mebane | 684 | 5.90% | 4 | |
| 9 | 11,574 | Dp. 5409 | 1332 | 11.50% | 3 | |

Figure 1:
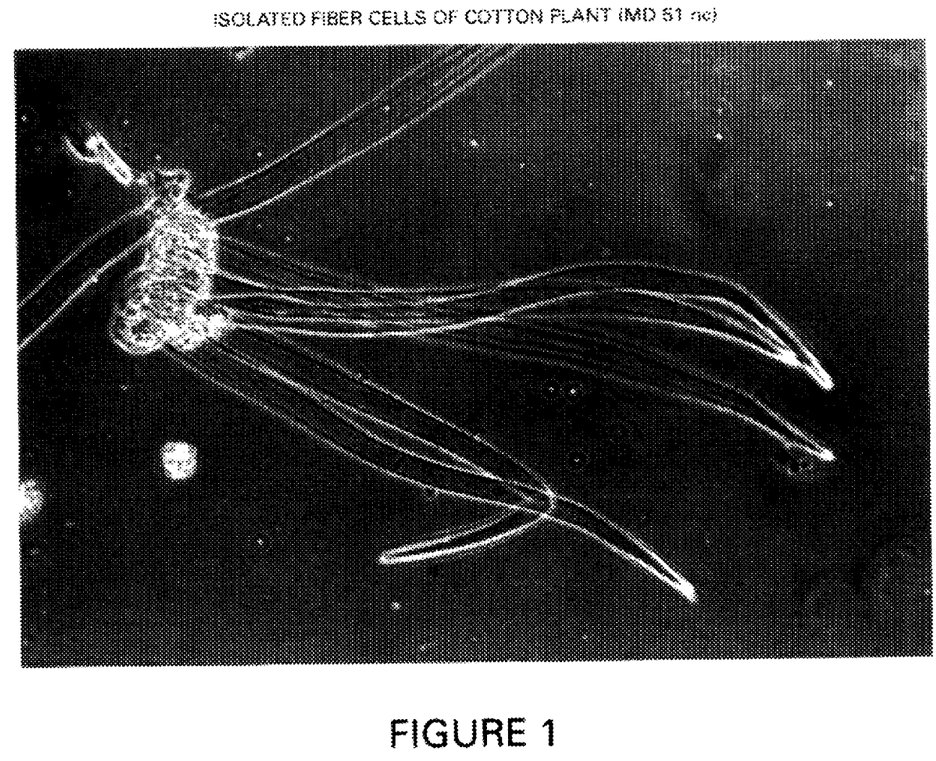
FIG. 1 is a microphotograph at 280 X magnification of a fiber cell isolated from a cotton plant (MD51 nc) in accordance with the method of the present invention.
Figure 2:
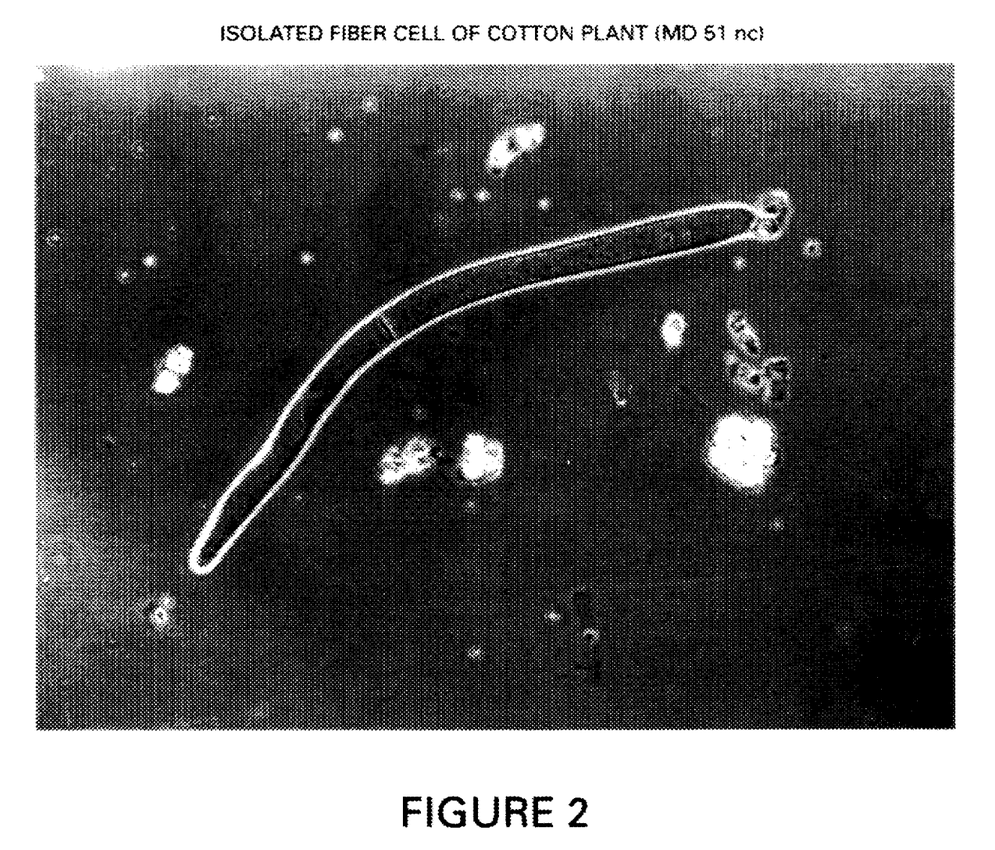
FIG. 2 is a microphotograph at 280 X magnification of a fiber cell isolated from a cotton plant (MD51 nc) in accordance with the method of the present invention.
Figure 3:
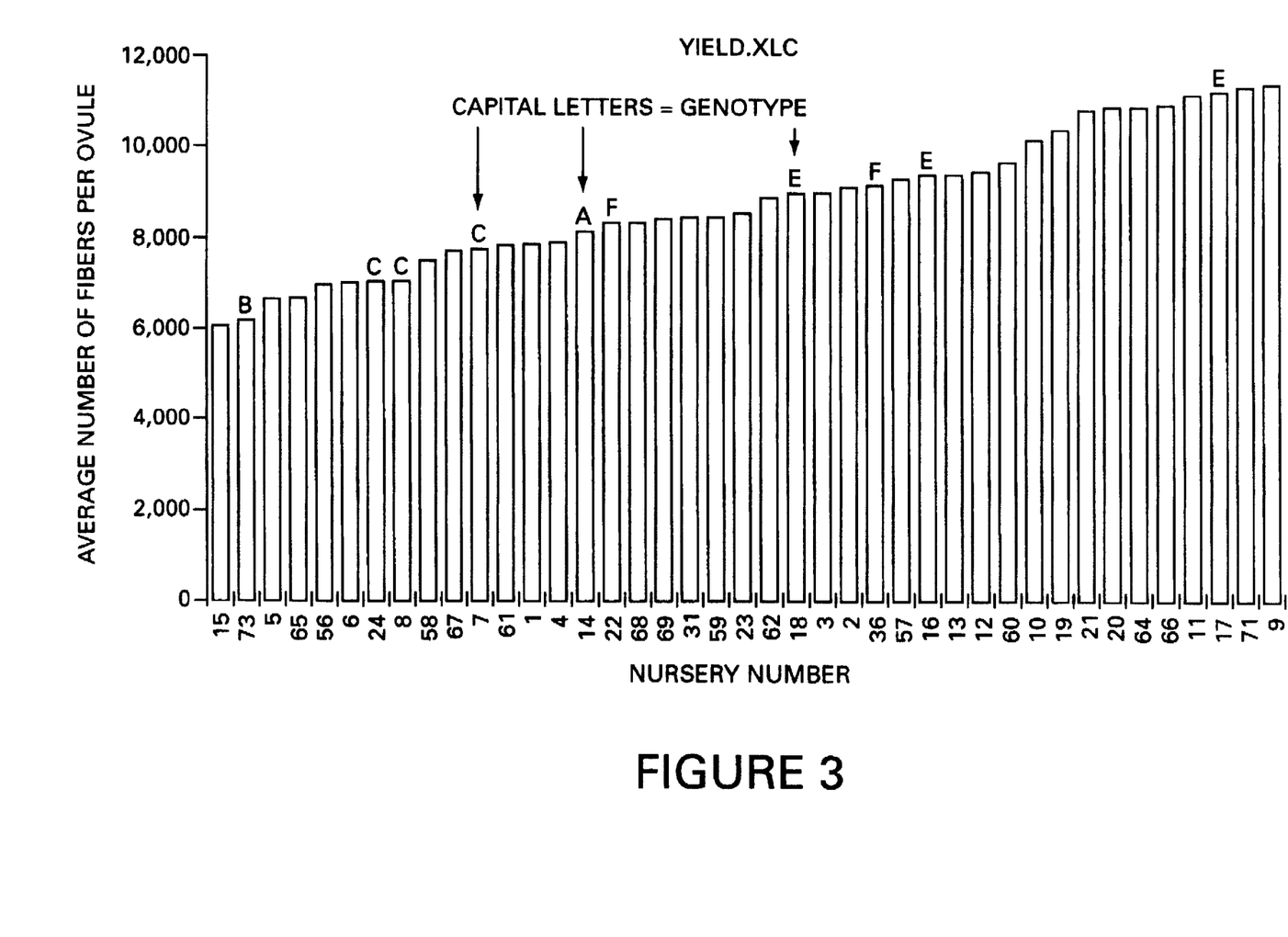
FIG. 3 is a graph which depicts the number of cells per ovule in various nursery plants grown in sub-optimal conditions.

From Table 3 and FIG. 3, it is readily apparent that physical properties of a wide variety of fiber cells from plants grown under sub-optimal field conditions can be ascertained. In addition, Table 3 illustrates that the numbers of cotton fiber cells per ovule of various cotton plants can be calculated with large percentage of accuracy. Specifically, through the utilization of the present invention, the numbers of fiber cells per of various cotton plants were estimated with only an average error of about 7% error.

In addition, Table 3 illustrates that different genotypes of the cells can also be determined before harvest. For example, nursery plant no. 14 was identified as genotype A; nursery plant no. 15 was identified as genotype B; nursery plant nos. 6, 8, and 7 were identified as genotype C; nursery plant no. 31 was identified as genotype D; nursery plant nos. 18, 16, and 17 were identified as genotype E; and nursery plant no. 36 was identified as genotype F. Thus, through the present invention, cotton growers can now determine the genotypes and characteristics of cotton plants prior to harvest.

Example 4

Cotton fiber cells were separated from cotton ovules obtained from 34 nursery plants in accordance with the method of the present invention. The numbers of cotton fiber cells per ovule from plants cultivated under optimal field conditions (i.e., warm weather and sunshine) were determined in accordance with the present invention. The physical properties of cotton plants observed are shown in Table 4 and depicted in FIG. 4.

TABLE 4

| Nursery Plant No. | Variety | Cells per Ovule | S.D. | % Error |
| --- | --- | --- | --- | --- |
| 1 | X 5402 | 10447 | 1261 | 12% |
| 2 | Dessi | 11160 | 189 | 2% |
| 3 | Deltapine 5415 | 11531 | 838 | 7% |
| 4 | Sure Grow 501 | 12272 | 814 | 7% |
| 5 | MD51 | 12504 | 1403 | 11% |
| 6 | Deltapine 5409 | 13005 | 851 | 7% |
| 7 | Deltapine 50 | 13111 | 428 | 3% |
| 8 | Deltapine 51 | 13142 | 182 | 1% |
| 9 | MS200 | 13482 | 1502 | 11% |
| 10 | Deltapine 20 | 13691 | 1391 | 10% |
| 11 | PM 145 | 13709 | 68 | 0% |
| 12 | Deltapine 5690 | 13947 | 1498 | 11% |
| 13 | X 402 | 14195 | 1367 | 10% |
| 14 | Pima 57 | 14324 | 1314 | 9% |
| 15 | 6101 | 14390 | 417 | 3% |
| 16 | X 404 | 14499 | 314 | 2% |
| 17 | X 5201 | 15121 | 1033 | 7% |
| 18 | 6102 | 15187 | 1032 | 7% |

TABLE 4-continued

| Nursery Plant No. | Variety | Cells per Ovule | S.D. | % Error |
|---|---|---|---|---|
| 19 | Deltapine 90 | 15458 | 449 | 3% |
| 20 | Sure Grow 125 | 15593 | 1095 | 7% |
| 21 | Stoneville 474 | 15844 | 1018 | 6% |
| 22 | Pima 3 | 16070 | 522 | 3% |
| 23 | X 405 | 16120 | 1250 | 8% |
| 24 | Hartz 1220 | 16127 | 956 | 6% |
| 25 | X 412 | 16628 | 261 | 2% |
| 26 | X 4101 | 16676 | 1808 | 11% |
| 27 | CA 3093 | 16752 | 378 | 2% |
| 28 | X 5601 | 17296 | 664 | 4% |
| 29 | Pima 1 | 17349 | 993 | 6% |
| 30 | Hartz 1244 | 17964 | 1319 | 7% |
| 31 | All Texas Atlas | 18535 | 368 | 2% |
| 32 | MS 26 | 19102 | 1565 | 8% |
| 33 | B&D Tejas | 21426 | 1296 | 6% |
| 34 | Pima 2 | 21597 | 1314 | 6% |

Figure 4:
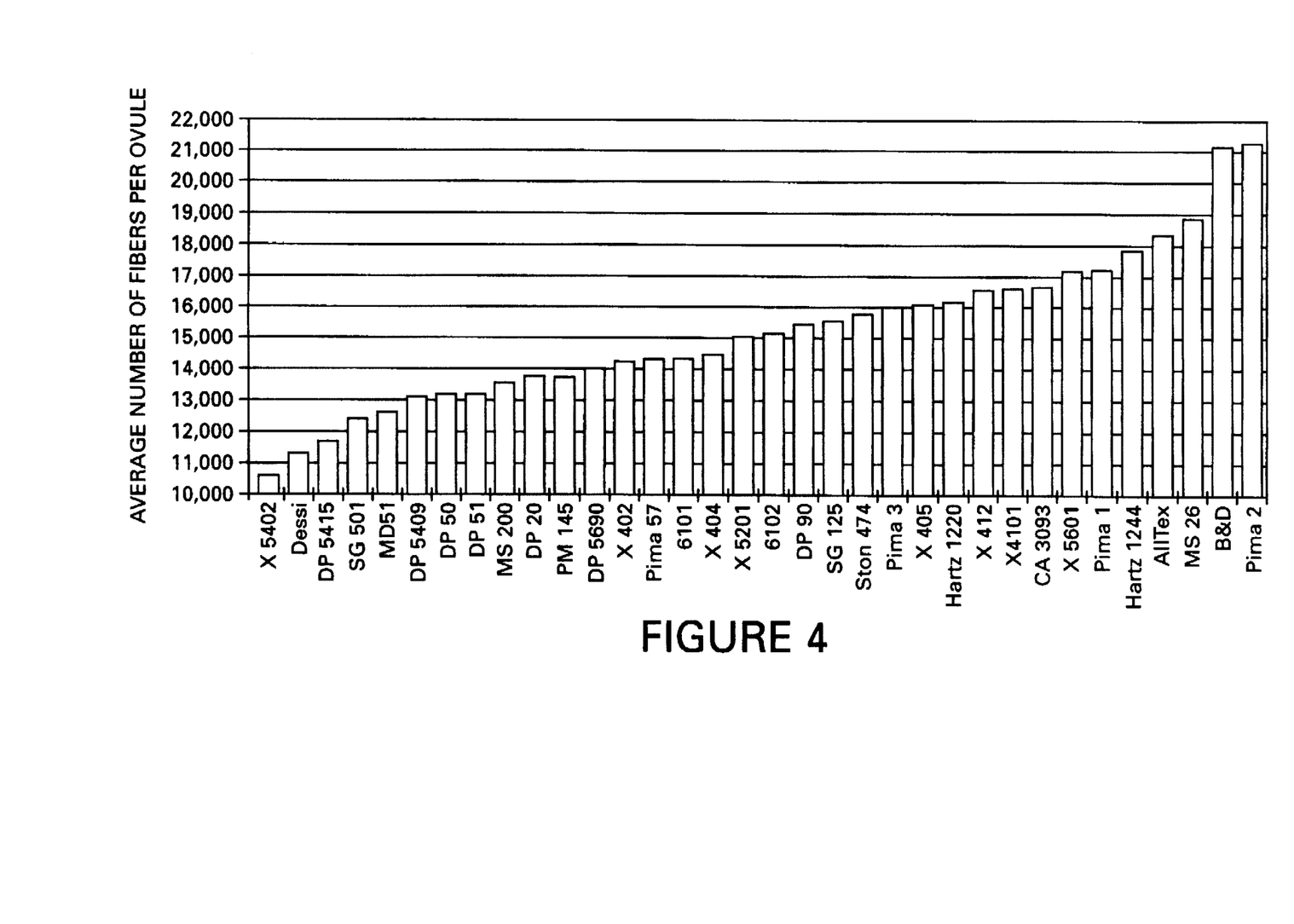
FIG. 4 is a graph which depicts the number of cells per ovule in various nursery plants grown in optimal conditions.

From Table 4 and FIG. 4, it is readily apparent that physical properties of a wide variety of fiber cells from plants grown under optimal field conditions can be ascertained. In addition, Table 4 illustrates that the numbers of cotton fiber cells per ovule of various cotton plants can be calculated with large percentage of accuracy. Specifically, the numbers of fiber cells per ovule of various cotton plants were estimated with only average error of about 6%.

Examples 5 to 8

Cotton fiber cells were separated from cotton ovules obtained from a varieties of nursery plants grown at different locations within the United States. The numbers of cotton fiber cells per ovule from plants cultivated under optimal field conditions (i.e., warm weather and sunshine) were determined in accordance with the present invention. The numbers of fiber cells per ovule from the cotton plants are shown in Tables 5 through 8.

TABLE 5

Fiber Cell Counts-Arkansas (Lewis) vs. North Carolina

| | North Carolina | | | Arkansas (Lewis) | | |
|---|---|---|---|---|---|---|
| Variety | Cells Per Ovule | S.D. | Sample No. | Cells Per Ovule | S.D. | Sample No. |
| DP 50 | 13549 | 600 | 3 | 13029 | 1893 | 4 |
| DP 5809 | 14904 | 431 | 3 | 13005 | 851 | 1 |
| Hartz 1220 | 15643 | 681 | 3 | 16127 | 956 | 1 |
| Hartz 1244 | 16413 | 709 | 3 | 17964 | 1319 | 1 |
| Sure Grow 501 | 14780 | 1107 | 3 | 12272 | 814 | 1 |
| Stoneville 474 | 15503 | 276 | 3 | 15844 | 1018 | 1 |
| SureGrow 125 | 15283 | 588 | 2 | 15593 | 1095 | 1 |

TABLE 6

North Carolina Fiber Cell Counts

| Variety | 1st week | 2nd week | 3rd week |
|---|---|---|---|
| DP 50 | 12785 | 14251 | 13611 |
| DP 5809 | 14732 | 15498 | 14484 |
| Hartz 1220 | 16246 | 15992 | 14691 |
| Hartz 1244 | 17267 | 15530 | 16444 |
| Sure Grow 501 | 14579 | 13536 | 16227 |

TABLE 6-continued

North Carolina Fiber Cell Counts

| Variety | 1st week | 2nd week | 3rd week |
|---|---|---|---|
| Stoneville 474 | 15725 | 15671 | 15114 |
| Sure Grow 125 | — | 15871 | 15283 |

TABLE 7

Arkansas (Lewis) Fiber Cell Counts

| Variety | 1st week | 2nd week | 3rd week | 4th week |
|---|---|---|---|---|
| DP 50 | 11162 | 11394 | 13772 | 15791 |

TABLE 8

Arkansas (Lewis) vs. North Carolina Fiber Cell Counts

| Variety | N.C. cnts. | Ark. cnts. | N.C. cnts. minus Ark. cnts |
|---|---|---|---|
| DP 50 | 13549 | 13029 | 520 |
| DP 5809 | 14904 | 13005 | 1899 |
| Hartz 1220 | 15643 | 16127 | −484 |
| Hartz 1244 | 16413 | 17964 | −1551 |
| SureGrow 501 | 14780 | 12272 | 2508 |
| Stoneville 474 | 15503 | 15844 | −341 |
| SureGrow 125 | 15283 | 15593 | −310 |

While there have described what are believed to be the preferred embodiments of the invention, those skilled in the art will realize that changes and modification may be made to the invention without departing from the spirit of such invention. All such changes and modifications will fall within the scope of the invention and are intended to be claimed.

What is claimed is:

1. A method of rendering cotton fiber cells that are post-anthesis and pre-harvest available for analysis of their physical properties, which comprises:
   (a) hydrolyzing cotton fiber cells on cotton ovules by the steps of
      (i) treating said ovules with a primary acid solution under conditions effective to hydrolyze the intercellular connections of said fiber cells on said ovules, and
      (ii) treating said fiber cells with a sulfur-containing reagent under conditions effective to increase the flexibility of said fiber cells; and
   (b) separating said fiber cells from said ovules thereby rendering said fiber cells available for analysis of their physical properties.

2. The method according to claim 1, wherein said primary acid solution is an acid solution having an inorganic acid with a pKa of at least about 7.

3. The method according to claim 2, wherein said inorganic acid is HCL.

4. The method according to claim 2, wherein said inorganic acid is selected from the group consisting of $HNO_3$, $H_2SO_4$, and $HClO_4$.

5. The method according to claim 1, wherein said sulfur-containing reagent is a meta-bisulfite.

6. The method according to claim 1, wherein said sulfur-containing reagent is sulfur dioxide.

7. The method according to claim 1, which further comprises treating said cotton ovules with a secondary acid solution prior to Step (i) for an effective amount of time to hydrolyze the intracellular contents of said fiber cells.

8. The method according to claim 7, wherein said secondary acid solution is an acid solution having acid with a pKa of least about 4.

9. The method according to claim 8, wherein said acid is glacial acetic acid.

10. The method according to claim 8, wherein said acid is selected from the group consisting of acetic acid, propionic acid, lactic acid, and formic acid.

11. The method according to claim 1, which further comprises the step of treating said cells with a fixative solution prior to separating said fiber cells from said ovules.

12. The method according to claim 11, wherein the step of treating said cells with a fixative solution comprises immersing said ovules and said fiber cells in said fixative solution.

13. The method according to claim 12, wherein said fixative solution comprises a solution of an alcohol and an acid.

14. The method according to claim 13, wherein said mixtures of said alcohol and said acid are in ratio ranging from about 10:1 to 1:10.

15. The method according to claim 13, wherein said alcohol of said fixative solution is ethanol.

16. The method according to claim 13, wherein said alcohol of said fixative solution is selected from the group consisting of methanol and propanol.

17. The method according to claim 13, wherein said acid of said fixative solution is glacial acetic acid.

18. The method according to claim 13, wherein said acid of said fixative solution is selected from the group consisting of acetic acid, propionic acid, lactic acid, and formic acid.

19. The method according to claim 1, wherein said separation comprises the steps of:

(a) removing cotton plant embryos from said ovules; and thereafter (b) isolating said fiber cells from said ovules whereby said fiber cells are rendered available for analysis.

20. The method according to claim 1, which further comprises treating said fiber cells with a tertiary acid solution prior to separating said fiber cells from said ovules.

21. The method according to claim 20, wherein said tertiary acid solution is an acid solution having an acid with a pKa of at least about 3.

22. The method according to claim 21, wherein said acid is selected from the group consisting of propionic acid, lactic acid, and acetic acid, and citric acid.

23. The method according to claim 21, wherein said acid is acetic acid.

24. The method according to claim 1, which further comprises the steps of:

(a) placing said fiber cells under a microscope; and (b) observing the physical properties of said fiber cells.

* * * * *